United States Patent
Calmes, Jr. et al.

(10) Patent No.: US 9,802,889 B2
(45) Date of Patent: Oct. 31, 2017

(54) SOLID SUPPORTED TRITHIOL COMPOUNDS FOR REMOVING HEAVY METALS FROM SOLUTION, AND FILTRATION SYSTEMS UTILIZING THE COMPOUNDS

(71) Applicant: Covalent Research Technologies, LLC, Mt. Pleasant, SC (US)

(72) Inventors: Robert Blalock Calmes, Jr., Lexington, KY (US); Rudolph C. Schmidt, Jr., Lexington, KY (US); Lisa Yvonne Blue, Georgetown, KY (US); Jared K. Nelson, Pisgah Forest, NC (US); Wesley A. Freund, Arden, NC (US); Peter W. Newsome, Mills River, NC (US)

(73) Assignee: Covalent Research Technologies, LLC, Mt. Pleasant, SC (US)

( * ) Notice: Subject to any disclaimer, the term of this patent is extended or adjusted under 35 U.S.C. 154(b) by 421 days.

(21) Appl. No.: 14/558,031

(22) Filed: Dec. 2, 2014

(65) Prior Publication Data
US 2016/0152563 A1    Jun. 2, 2016

(51) Int. Cl.
C07C 323/42    (2006.01)
C02F 1/28    (2006.01)
(Continued)

(52) U.S. Cl.
CPC .............. *C07C 323/42* (2013.01); *B01J 20/22* (2013.01); *C02F 1/285* (2013.01); *C02F 1/42* (2013.01);
(Continued)

(58) Field of Classification Search
None
See application file for complete search history.

(56) References Cited

U.S. PATENT DOCUMENTS 5,073,575 A    12/1991    Blanch et al.
6,586,600 B2    7/2003    Atwood et al.
(Continued)

FOREIGN PATENT DOCUMENTS

CN    101898824 A    12/2010
CN    102531137 A    7/2012
(Continued)

*Primary Examiner* — Taiwo Oladapo
(74) *Attorney, Agent, or Firm* — Dinsmore & Shohl LLP

(57) ABSTRACT

Solid-supported trithiol compounds are prepared. The solid-supported trithiol compounds have formula (I):

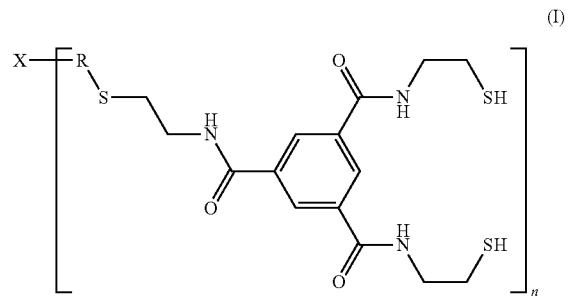

in which R is a linker moiety, X is a solid support, and n≥1. The compounds of formula (I) may be incorporated into methods for removing heavy metals from solutions and into batch systems or filtration apparatus that remove heavy metals from solutions.

20 Claims, 4 Drawing Sheets

(51) Int. Cl.
  *C02F 1/42*   (2006.01)
  *B01J 20/22*  (2006.01)
  *C02F 101/10* (2006.01)
  *C02F 101/20* (2006.01)
  *C02F 101/38* (2006.01)
  *C02F 103/10* (2006.01)

(52) U.S. Cl.
  CPC .. *C02F 2101/103* (2013.01); *C02F 2101/203* (2013.01); *C02F 2101/38* (2013.01); *C02F 2103/10* (2013.01); *C07B 2200/11* (2013.01)

(56) References Cited

U.S. PATENT DOCUMENTS

| | | |
|---|---|---|
| 6,852,369 B1 | 2/2005 | Atwood |
| 2011/0076246 A1 | 3/2011 | Haley et al. |
| 2011/0160150 A1 | 6/2011 | Haley et al. |

FOREIGN PATENT DOCUMENTS

| | | |
|---|---|---|
| CN | 102531138 A | 7/2012 |
| CN | 101898824 B | 10/2012 |
| CN | 102531137 B | 1/2014 |
| EP | 2471654 A2 | 7/2012 |
| JP | 2001-40256 | 2/2001 |
| WO | 2012090639 A1 | 7/2012 |

SOLID SUPPORTED TRITHIOL COMPOUNDS FOR REMOVING HEAVY METALS FROM SOLUTION, AND FILTRATION SYSTEMS UTILIZING THE COMPOUNDS

TECHNICAL FIELD

This specification relates generally to compounds for removing heavy metals from solutions and to filtration systems utilizing the compounds, and, more specifically, to solid-supported trithiol compounds, methods of making the solid-supported trithiol compounds, methods for removing heavy metals from solutions using the solid-supported trithiol compounds, and filtration systems such as batch systems and filtration apparatus that utilize the solid-supported trithiol compounds.

BACKGROUND

As a class of environmentally concerning contaminant elements, heavy metals include transition metals and metalloids. Heavy metals are often discharged into the environment through, for example, industrial process waters, mining effluents, organic wastes, and waste burning. Heavy metals can be toxic, even at low levels, to humans, animals, and plants. For environmental, public health, and economic reasons, it may be beneficial to efficiently and safely remove the heavy metals from the solution sources.

There remain ongoing needs for chemical compounds capable of removing heavy metals from solution streams or waters. There remain further needs for methods for preparing such compounds, methods for removing heavy metals from solutions by using such compounds, filtration apparatus, and methods such as batch methods that use such compounds as an active ingredient.

SUMMARY

According to some embodiments, a solid-supported trithiol compounds for use in removing heavy metals from solutions have formula (I):

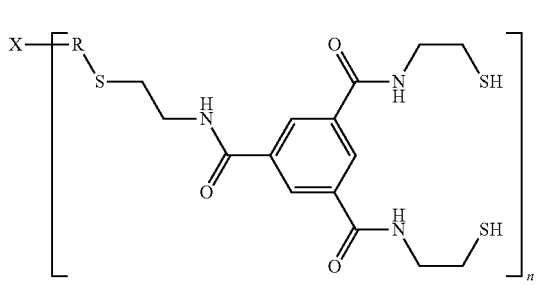

(I)

in which R is a linker moiety, X is a solid support, and $n \geq 1$.

According to some embodiments, a method for preparing a solid-supported trithiol compound may include reacting trimesic acid and cysteamine to form N,N',N''-tris(2-sulfanylethyl)benzene-1,3,5-tricarboxamide; and reacting the benzene-N,N',N''-tris(2-sulfanylethyl)benzene-1,3,5-tricarboxamide with a surface modified or functionalized solid support X to form a compound having formula (I).

According to further embodiments, methods for removing heavy metals present in solutions may include contacting a heavy metal-containing solution with a compound of formula (I) such that the compound binds with one or more heavy metals present in the heavy metal-containing solution.

According to further embodiments, filtration apparatus for removal of heavy metals from solutions may include a filter housing having a filter inlet through which a heavy-metal containing solution may be introduced, and a filter outlet through which a filtered solution may exit. The filtration apparatus may contain a filtration material that is made from or includes an active compound having formula (I), such that the heavy-metal containing solution contacts or flows through the active compound between entering the filter inlet and exiting the filter outlet.

According to further embodiments, a batch system for removing heavy metals from solutions may include a containment vessel having a stirring device, an inlet through which a heavy-metal containing solution may be introduced, and an outlet with a control valve through which a slurry comprising the heavy metals bound to an active compound having the formula (I) may exit.

Additional features and advantages of the embodiments for solid-supported trithiol compounds, methods and uses thereof described herein will be set forth in the detailed description that follows, and in part will be readily apparent to those skilled in the art from that description or recognized by practicing the embodiments described herein.

Both the foregoing general description and the following detailed description describe various embodiments and are intended to provide an overview or framework for understanding the nature and character of the claimed subject matter. The chemical structures disclosed are included to provide a further understanding of the various embodiments. The chemical structures illustrate the various embodiments described herein, and together with the description serve to explain the principles and operations of the claimed subject matter.

DETAILED DESCRIPTION

Figure 1:
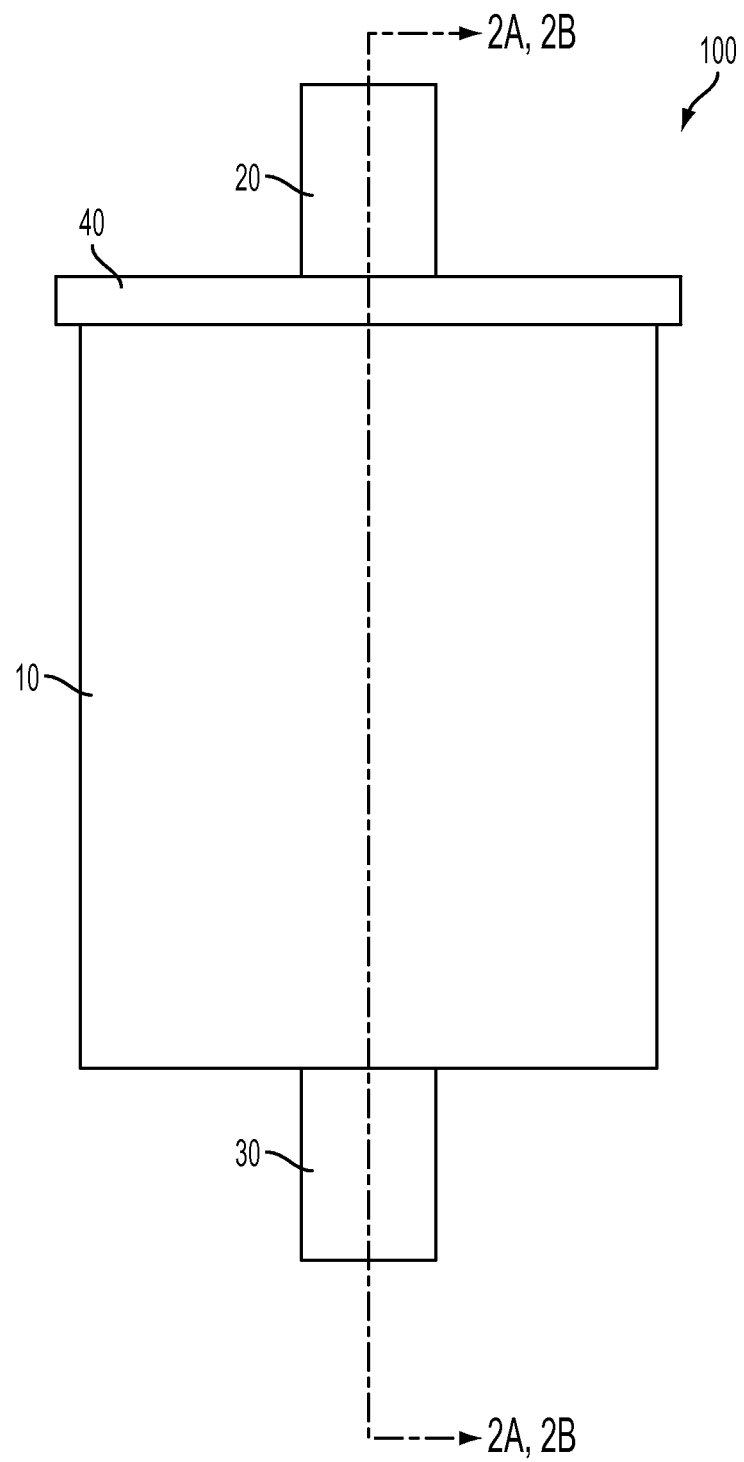
FIG. 1 is an elevation view of a heavy-metal removal system configured as a filtration apparatus containing a solid-supported trithiol compound, according to embodiments herein.

Reference will now be made in detail to embodiments of solid-supported trithiol compounds, methods for making these solid-supported trithiol compounds, methods for removing heavy metals from solution using the solid-supported trithiol compounds, methods for recovering heavy metals from spent solid-supported trithiol compounds, and filtration apparatus comprising the solid-supported trithiol compounds.

As used herein, the term "heavy metal" refers to any transition metal or metalloid, particularly to any transition metal or metalloid that poses an environmental or health concern when present in a water source, stream, aquifer, or municipal water supply. Non-limiting examples of heavy metals include transition metals such as mercury, cadmium, copper, lead, and zinc; and metalloids such as arsenic. Additional examples of heavy metals that may have environmental concerns at varying levels include iron, chromium, cobalt, nickel, selenium, silver, antimony, and thallium.

According to some embodiments, solid-supported trithiol compounds may have formula (I):

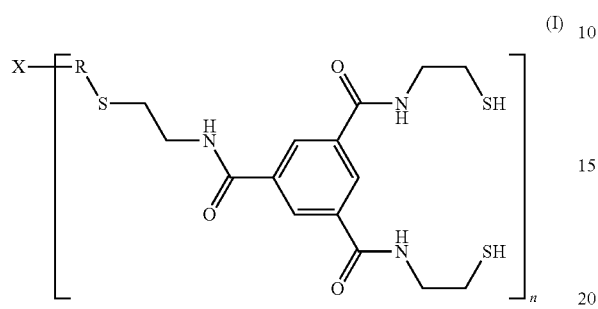

(I)

In formula (I), R is a linker moiety, and X is a solid support. According to some embodiments, the linker moiety R may covalently link a trithiol compound to the solid support X. It should be appreciated by the skilled artisan that a variety of linker moieties may be used to covalently bond the trithiol compound to the solid support. Linker moieties may be selected according to criteria such as, length, chemical stability, and chemical reactivity toward a thiol group.

With respect to formula (I), the solid support X may be any solid or water-insoluble material having suitable chemical stability and chemical reactivity to covalently bind with the linker moiety R. In some embodiments, the solid support may be a particle such as a bead, a wafer, or a chip. In other embodiments, the solid support X may be a surface such as a plate, a mesh, or a fabric. In exemplary embodiments, the solid support X may be a compound or material including, but not limited to, silica or silica beads, surface-modified silica or silica beads, functionalized silica or silica beads, alumina, alumina beads, polyethylene, polypropylene, polyvinylchloride, polystyrene, polystyrene copolymers, polyacrylamides, polymethacrylates, polysaccharides, phenolic resins, polymer beads, carbon, activated carbon, carbon black, graphite, or combinations of any of these.

In some embodiments, the linker moiety R may be a hydrocarbon group, in which one or more carbon atoms optionally may be replaced with a heteroatom such as oxygen, nitrogen, or a halogen. The hydrocarbon group may be a straight-chain group or branched group and may contain a cyclic group or an aromatic group, any of which optionally may be substituted with heteroatoms or with groups such as hydroxyls, carbonyls, amines, or nitro groups, for example. In some embodiments, the hydrocarbon group may contain from 1 to 20 or from 1 to 10 carbon atoms. In illustrative embodiments, the linker moiety R may be chosen from any of the following structures (a)-(e), where in structures (a) and (d) according to various embodiments, x is from 1 to 10, from 1 to 5, from 2 to 10, from 2 to 5, from 3 to 10, or from 3 to 5, or equal to 3):

—(CH$_2$)$_x$— (a)

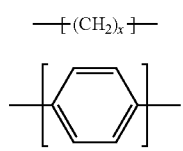
(b)

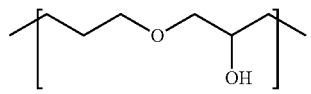
(c)

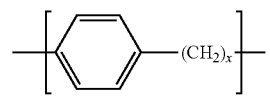
(d)

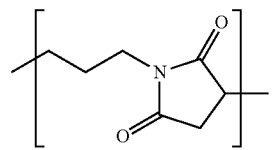
(e)

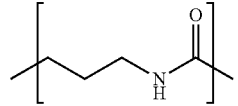
(f)

In some embodiments, the solid support X may be a material that has been surface-modified or functionalized with precursors to the linking moiety R. Such a surface-modified or functionalized solid support X may be represented by formula (II):

(II)

In formula (II), X is the solid support; Q is a precursor to the linking moiety (R in the solid-supported trithiol compound of formula (I)), and n≥1. The surface-modified or functionalized compound of formula (II) may be reacted with a trithiol. For example, the material of formula (II) may be reacted with a trithiol having formula (III):

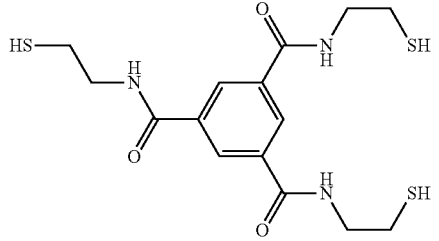

(III)

Thus, in some embodiments, the solid-supported trithiol compound of formula (I) may be formed by the reaction of the surface-modified or functionalized material of formula (II) with the trithiol compound of formula (III). In some embodiments, the solid support X may be surface-modified or functionalized with a precursor functionality Q that covalently bonds to the solid support X and also is chemically reactive to thiol groups of the trithiol compound of formula (III), such that reaction of the surface-modified or functionalized solid support X results in the trithiol compound linked to the solid support X through the linking moiety R. In such a reaction, the precursor functionality Q forms the structural backbone of the linking moiety R. In exemplary embodiments, the solid support may be silica, such as silica beads, for example. The silica may be functionalized with using an organosilane compound having organic groups that are reactive to thiols. These organic groups then react with a thiol group of the trithiol compound to become the linker moiety.

In the solid-supported trithiol compounds of formula (I), the linker moiety R may be formed from a precursor functionality Q bound to the solid support X. The precursor functionality Q may be chosen from any organic group capable of bonding covalently to both the trithiol compound and the solid support, so as to covalently link the trithiol compound to the solid support X when the trithiol compound is reacted with the precursor functionality Q. According to some embodiments, examples of precursor functionality Q may include, without limitation, hydrocarbon groups, alkyls, substituted alkyls, alkenyls, substituted alkenyls, heterocyclic groups, polycyclic groups, alkoxyl groups, substituted alkoxyl groups, aryl groups, or substituted aryl groups. Further examples of precursor functionality Q may include alkyl groups with heteroatom substitutions, particularly oxygen or nitrogen. Alkyl groups with heteroatom substitutions may include aldehydes, ketones, ethers, esters, glycols, alcohols, amino groups, substituted amino groups, carbonyl groups, or combinations thereof.

Examples of suitable alkyl groups that may form the precursor functionality Q may include, but are not limited to, straight-chain alkyl groups, branched-chain alkyl groups, cycloalkyl (alicyclic) groups, alkyl substituted cycloalkyl groups, and cycloalkyl substituted alkyl groups. The alkyl groups may further include both unsubstituted alkyls and substituted alkyls (which can include cycloalkyls). In substituted alkyls, a hydrogen atom on one or more carbons of the hydrocarbon backbone, may be replaced with, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It should be understood by those skilled in the art that the moieties substituted on the hydrocarbon chain can themselves be substituted. In some embodiments, the precursor functionality Q may be a straight chain or branched chain alkyl having from about 1 to about 30 carbon atoms in its backbone. In other embodiments, the precursor functionality Q may be a straight chain or branched chain alkyl having from about 1 to about 15 carbon atoms in its backbone.

Examples of suitable alkenyl groups that may form the precursor functionality Q may include, but are not limited to, straight-chain alkenyl groups or branched-chain alkenyl groups, cycloalkenyl (alicyclic) groups, alkyl substituted cycloalkenyl groups, and cycloalkyl substituted alkenyl groups. The alkenyl groups may further include both unsubstituted alkenyls and substituted alkenyls (which can include cycloalkenyls). In substituted alkenyls, a hydrogen atom on one or more carbons of the hydrocarbon backbone, may be replaced with, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It should be understood by those skilled in the art that the moieties substituted on the hydrocarbon chain can themselves be substituted. In some embodiments, the precursor functionality Q may be a straight chain or branched chain alkenyl having from about 2 to about 30 carbon atoms in its backbone. In other embodiments, the precursor functionality Q may be is a straight chain or branched chain alkenyl having from about 2 to about 15 carbon atoms in its backbone.

Examples of suitable alkynyl groups that may form the precursor functionality Q may include, but are not limited to, straight-chain alkynyl groups, branched-chain alkynyl groups, cycloalkynyl (alicyclic) groups, alkyl substituted cycloalkynyl groups, and cycloalkyl substituted alkynyl groups. The alkynyl groups may further include both unsubstituted alkynyls and substituted alkynyls (which can include cycloalkynyls). In substituted alkynyls, a hydrogen atom on one or more carbons of the hydrocarbon backbone, may be replaced with, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It should be understood by those skilled in the art that the moieties substituted on the hydrocarbon chain can themselves be substituted. In some embodiments, the precursor functionality Q may be a straight chain or branched chain alkynyl having from about 2 to about 30 carbon atoms in its backbone. In other embodiments, the precursor functionality Q may be a straight chain or branched chain alkynyl having from about 2 to about 15 carbon atoms in its backbone.

Examples of suitable aryl groups that may form the precursor functionality Q may include, but are not limited to, 5-membered or 6-membered single-ring aromatic groups that may include from zero to four heteroatoms, such as, benzene, pyrrole, furan, thiophene, imidazole, benzoxazole, benzothiazole, triazole, pyrazole, pyridine, pyrazine, pyridazine and pyrimidine, and the like. Aryl groups may further include polycyclic fused aromatic groups such as naphthyl, quinolyl, indolyl, and the like. The aromatic ring may be substituted at one or more ring positions with such substituents such as, for example, halogen, hydroxyl, alkyl (may also be called alkylaryl), alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. In some embodiments, the precursor functionality Q may be an alkylaryl moiety. In other embodiments, the precursor functionality Q may be a phenylmethyl moiety.

Examples of suitable heterocyclyl groups that may form the precursor functionality Q may include, but are not limited to, 3-membered to 10-membered ring structures containing one to four heteroatoms. Examples of heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring may also be substituted at one or more positions with halogen, hydroxyl, alkyl (may also be called a heteroalkyl moiety) alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

Examples of suitable polycyclyl groups that may form the precursor functionality Q may include, but are not limited to, cycloalkyls, cycloalkenyls, cycloalkynyls, aryls and/or heterocyclyls in which two or more carbons are common to two adjoining rings such that the rings are fused rings. In some embodiments, the rings may be bridged rings such that two non-adjacent carbon atoms are common to each ring. In some embodiments, the rings may have two adjacent carbon atoms common to each ring. In embodiments herein, each of the rings of the polycyclyl can be substituted with halogen, hydroxyl, alkyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

Examples of suitable alkoxy groups that may form the precursor functionality Q may include, but are not limited to, alkoxy groups having a carbon backbone chain. The alkoxy group may be branched or unbranched and saturated or unsaturated. In some embodiments, the alkoxy groups may further include both unsubstituted alkoxy groups and substituted alkoxy groups (which can include cycloalkoxy groups). In substituted alkoxy groups, a hydrogen atom on one or more carbons of the hydrocarbon backbone, may be replaced with, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It should be understood by those skilled in the art that the moieties substituted on the hydrocarbon chain can themselves be substituted. In some embodiments, the precursor functionality Q may be a straight chain or branched chain alkoxy having from about 1 to about 30 carbon atoms in its backbone. In other embodiments, the precursor functionality Q may be a straight chain or branched chain alkoxy having from about 1 to about 15 carbon atoms in its backbone.

Examples of suitable amino groups that may form the precursor functionality Q may include, but are not limited to, nitrogen atoms attached by single bonds to hydrogen atoms, alkyl groups, aryl groups, or a combination thereof. In some embodiments, the amino group is a primary, secondary or tertiary amino group. In other embodiments, the amino group may be a cyclic amino group. The amino groups may be substituted with, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It should be understood by those skilled in the art that the moieties substituted on the amino group can themselves be substituted.

Examples of suitable carbonyl compounds that may form the precursor functionality Q may include, but are not limited to, aldehydes, including, for example, substituted or unsubstituted linear aldehydes, branched aldehydes, and/or cyclic aldehydes, ketones, including, for example, substituted or unsubstituted diketones, cyclic ketones, and/or unsaturated ketones, carboxylic acid, and carboxylic acid derivatives (e.g., esters, thioesters, amides. acyl halides, acid anhydrides, carboxylates). In general, carbonyl groups have a carbon atom double bonded to an oxygen atom. Carbonyl groups may be bonded to other functional groups to form carbonyl compounds.

In some embodiments, the precursor functionality Q may be chosen from ω-chloroalkyl groups or ω-bromoalkyl groups having from 3 to 10 carbon atoms, glycidoxy groups, chlorophenyl or bromophenyl groups, benzyl groups having chloro or bromo substitution on the benzylic carbon atom, maleimide groups, or N-alkylmaleimide groups. Examples of ω-chloroalkyl groups or ω-bromoalkyl groups include, without limitation, 3-chloropropyl, 3-bromopropyl, 4-chlorobutyl, 4-bromobutyl, 5-chloropentyl, 5-bromopentyl, 6-chlorohexyl, 6-bromohexyl, 7-chloroheptyl, 7-bromoheptyl, 8-chlorooctyl, 8-bromooctyl, 9-chlorononyl, 9-bromononyl, 10-chlorodecyl, and 10-bromodecyl. Examples of chlorophenyl or bromophenyl groups may include, without limitation 4-chlorophenyl and 4-bromophenyl. Examples of benzyl groups may include 4-(chloromethyl)phenyl and 4-(bromomethyl)phenyl. Non-limiting illustrative embodiments of materials according to formula (II) including the precursor functionality Q, and the solid-supported trithiol compounds according to formula (I) by reacting the material according to formula (II) with the trithiol of formula (III) are provided in TABLE 1 below.

TABLE 1

Exemplary solid-supported trithiol compounds and functionalized solid supports that may be used to prepare the compounds

| Ref. | Material of Formula (II) | Solid Supported Trithiol of Formula (I) |
|---|---|---|
| 1 | X–[–CH₂CH₂CH₂–Br]$_n$ or X–[–CH₂CH₂CH₂–Cl]$_n$ | (structure shown) |
| 2 | X–[–C₆H₄–Br]$_n$ or X–[–C₆H₄–Cl]$_n$ | (structure shown) |
| 3 | X–[–C₆H₄–CH₂Br]$_n$ or X–[–C₆H₄–CH₂Cl]$_n$ | (structure shown) |
| 4 | X–[–CH₂CH₂CH₂–O–CH₂–(epoxide)]$_n$ | (structure shown) |

TABLE 1-continued

Exemplary solid-supported trithiol compounds and functionalized solid supports that may be used to prepare the compounds

| Ref. | Material of Formula (II) | Solid Supported Trithiol of Formula (I) |
| --- | --- | --- |
| 5 | [structure: X—(propyl)—N-maleimide]$_n$ | [structure: X—(propyl)—N-succinimide-S-CH$_2$CH$_2$—NH—C(O)—benzene-1,3,5-tricarboxamide with two —NH—CH$_2$CH$_2$—SH arms]$_n$ |
| 6 | [structure: X—(propyl)—N=C=O]$_n$ | [structure: X—(propyl)—NH—C(O)—S—CH$_2$CH$_2$—NH—C(O)—benzene-1,3,5-tricarboxamide with two —NH—CH$_2$CH$_2$—SH arms]$_n$ |

Referring to TABLE 1, reference compound 1 of formula (I) may formed from a solid support having 3-bromopropyl or 3-bromochloro precursor functionalities. Reference compound 2 of formula (I) may be formed from a solid support having 4-bromophenyl or 4-chlorophenyl precursor functionalities. Reference compound 3 of formula (I) may be formed from a solid support having 4-(bromomethyl)phenyl or 4-(chloromethyl)phenyl precursor functionalities. Reference compound 4 of formula (I) may be formed from a solid support having glycidoxy precursor functionalities. Reference compound 5 of formula (I) may be formed from a solid support having N-propylmaleimido precursor functionalities. Reference compound 6 of formula (I) may be formed from a solid support having N-propylisocyanate precursor functionalities According to some embodiments, the compound of formula (I) may include solid supported trithiol compounds, in which the trithiol compounds present on the solid support may be linked to the solid support by more than one type of linker moiety R. For example, the compound of formula (I) may include a first portion of trithiols linked to the solid support X via a linker moiety formed from a 3-bromopropyl precursor functionality and a second portion of trithiols linked to the solid support X via a linker moiety formed from a 4-(bromomethyl)phenyl precursor functionality.

In the surface-modified or functionalized materials of formula (II) and the solid-supported trithiol compounds of formula (I), the subscript n refers to a number of trithiol compounds of formula (III) that are linked through the linker moiety R to a single solid support X. In general, the subscript n≥1. Thus, if the solid support is a silica bead, for example, a corresponding material of formula (II) would include the silica bead with at least one precursor functionality Q bonded to a surface of the silica bead. Likewise, a corresponding solid-supported thiol compound according to formula (III) would include the silica bead with at least one trithiol compound according to formula (III) bonded to the surface of the silica bead through a linker moiety R. As described above, the linker moiety R may result from the reaction of the precursor functionality Q with a trithiol compound of formula (III).

The subscript n in the compounds of formula (I) and the materials of formula (II) may be related to the level of surface modification or functionalization attainable by through chemically bonding precursor functionalities Q to the surface of the solid support X. Physical characteristics of the solid support X such as particle size and/or surface area may affect the attainable level surface modification or functionalization, for example. According to some embodiments, the material of formula (II) may be surface-modified or functionalized with a precursor functionality such that the subscript n represents a number of precursor functionalities on the solid support sufficient to result in from about 0.01 mmol to about 10 mmol of precursor functionalities per gram of solid support material and a surface coverage of from about 0.01 µmol to about 10 µmol of precursor functionalities per m$^2$ of surface area of the solid support. Owing to increased steric effects when the trithiol compound is bonded to the solid support, as compared to when only the precursor functionality is bonded to the solid support, the subscript n of the solid-supported trithiol compound of formula (I) may be lower than the subscript n of the material of formula (II) used to form the solid-supported trithiol. In a non-limiting exemplary embodiments, a solid-supported trithiol compound of formula (I) having a silica bead as a solid support X and a linker moiety R derived from 4-(chloromethyl)phenyl precursor functionalities Q may have a subscript n sufficient to result in from about 0.01 mmol to about 5 mmol of trithiol compound per gram of solid support material, from about 0.01 mmol to about 2 mmol of trithiol compound per gram of solid support material, from about 0.01 mmol to about 1 mmol of trithiol compound per gram of solid support material, or from about 0.1 mmol to about 0.5 mmol of trithiol compound per gram of solid support material.

A particularly useful class of surface modified or functionalized materials of formula (II) includes SiliaBond® functionalized silica gels, available from SiliCycle® of Quebec City, Quebec, Canada. The SiliaBond® gels contain silica particles or beads functionalized with organic groups that may be reactive with thiols in an amount sufficient to provide a thiol-supported compound of formula (I) with suitable activity toward removing heavy metals from waste waters or other solutions.

Embodiments of the solid-supported trithiol compounds have been described above. Exemplary embodiments of methods for synthesizing the solid-supported trithiol compound will now be described. According to some embodiments, a solid-supported trithiol compound having formula (I) may be prepared by reacting trimesic acid (benzene-1,3,5-tricarboxylic acid) and cysteamine (2-aminoethanethiol) to form a compound of formula (III), namely N,N',N"-tris(2-sulfanylethyl)benzene-1,3,5-tricarboxamide, as shown below:

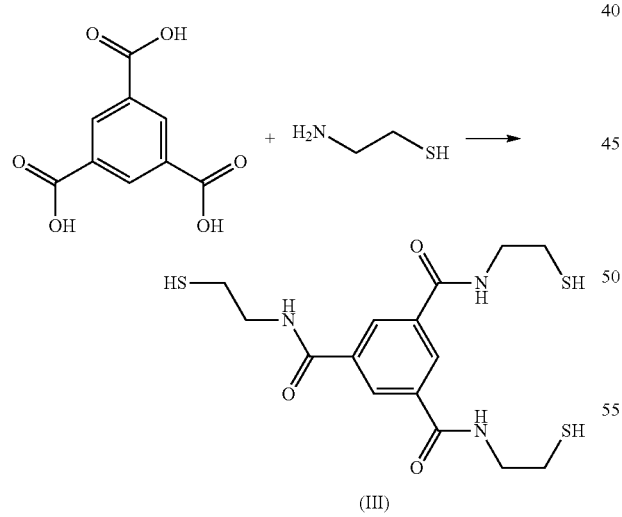

In some embodiments, carbonyldiimidazole may be added in an sufficient amount to activate the trimesic acid as it reacts with the cysteamine.

The N,N',N"-tris(2-sulfanylethyl)benzene-1,3,5-tricarboxamide may then be reacted with a functionalized material of formula (II) to form a solid-supported trithiol compound according to formula (I), as shown below:

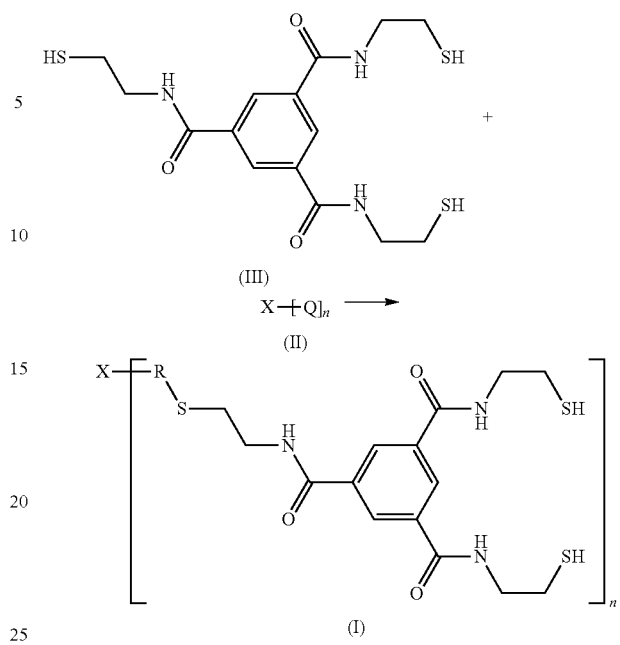

Groups X, R, Q, and subscript n in formula (I), formula (II), and formula (III) may be chosen from any of the groups described above with regard to embodiments of the solid-supported trithiol compounds.

The solid-supported trithiol compounds according to formula (I) may be used as active compounds for removal of heavy metals from solutions such as aqueous solutions, industrial process waters, mining effluents, and organic waste streams, for example. In some embodiments, the heavy metals may include arsenic, cadmium, copper, lead, mercury, zinc, or combinations thereof. In further embodiments, compounds that remove heavy metals from a solution may include a solid support having a support surface. The solid support of the compounds that remove heavy metals from a solution may be a compound or material including, but not limited to, silica or silica beads, surface-modified silica or silica beads, functionalized silica or silica beads, alumina, alumina beads, polyethylene, polypropylene, polyvinylchloride, polystyrene, polystyrene copolymers, polyacrylamides, polymethacrylates, polysaccharides, phenolic resins, polymer beads, carbon, activated carbon, carbon black, graphite, or combinations of any of these.

In the compounds that remove heavy metals from a solution the support surface is functionalized with a composition according to formula (IV):

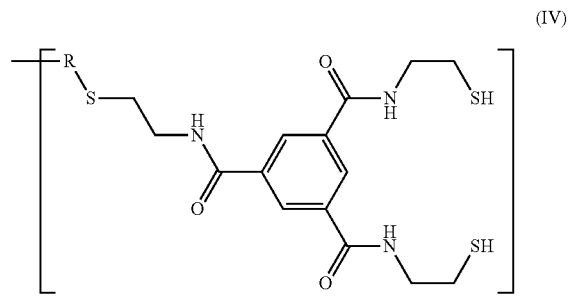

In formula (IV), group R is a linker moiety, as described above with respect to the solid-supported trithiol compounds of formula (I). The functionalization of the support surface may be afforded through covalent bonding of the compound of formula (IV) to the support surface through the linker moiety R. As described above, in some embodiments, the compound of formula (IV) may be formed by reacting a trithiol compound according to formula (III) with a functionalized material according to formula (II). In some embodiments, the support surface may be functionalized with the compounds of formula (IV) such that from about 0.01 mmol to about 5 mmol of the compound of formula (IV) is bonded to each gram of solid support material, from about 0.01 mmol to about 2 mmol of the compound of formula (IV) is bonded to each gram of solid support material, from about 0.01 mmol to about 1 mmol of the compound of formula (IV) is bonded to each gram of solid support material, or from about 0.1 mmol to about 0.5 mmol of the compound of formula (IV) is bonded to each gram of solid support material.

In some embodiments, the support surfaces of the compounds that remove heavy metals and metalloids from a solution may be functionalized by more than one compound of formula (IV), in which the compounds of formula (IV) are distinguishable by different linker moieties R. In other embodiments, the compounds that remove heavy metals and metalloids from a solution may include mixtures of solid support materials, in which a first portion of the solid support material is functionalized with a compound of formula (IV) having a first linker moiety R and a second portion of the solid support material is functionalized with a compound of formula (IV) having a second linker moiety R different from the first linker moiety.

According to further embodiments, methods for removing heavy metals present in a solution containing heavy metals may include contacting the solution with a compound having formula (I), as described above. The heavy metals may bind with the compounds described herein to form a compound—metal complex. In exemplary embodiments, the heavy metals may include, for example, mercury, arsenic, cadmium, copper, lead, zinc, or combinations thereof. The methods may further include adding one or more complexes of a chelator and a heavy metal or one or more complexes of a chelating agent and a heavy metal. When one or more such complexes is added to the solution, the heavy metals of the complexes may preferentially bind to the solid-supported compounds of formula (I) to form a more stable complex than the chelator or chelating agent complex added to the solution. In some embodiments, the methods may include adding a chelator-copper complex or a chelator-cadmium complex to the solution, such that copper or cadmium may preferentially bind to the solid-supported compounds of formula (I) and be removed from the solution. In illustrative embodiments, chelators such as ethylenediamine-tetraacetic acid (EDTA), N-(hydroxyethyl)-ethylenediaminetriacetic acid, ethylene glycol tetraacetic acid, diethylenetriaminepentaacetic acid, nitrilotriacetic acid, diethylenetriamine penta(methylene phosphonic acid), dimercaptosuccinic acid, 2,3-dimercapto-1-propanesulfonic acid, or combinations thereof, may be used to form the chelator-metal complexes.

Once the compounds of formula (I) are spent from binding with the heavy metals, in embodiments herein, the heavy metals may be recovered, thereby regenerating the solid-supported trithiol compound. Examples of heavy metals that may be recovered from the compounds described herein include, for example, mercury, arsenic, cadmium, copper, lead, and/or zinc. Regeneration of the solid-supported thiol compounds may be accomplished by any chemically suitable method, such as by heating or by exposing the compounds to an acidic or basic medium in which the heavy metal is soluble.

Solid-supported trithiol compounds, methods for their preparation, and methods for removing heavy metals from solution using the compounds have been described above. Embodiments of heavy-metal removal systems including the solid-supported trithiol compounds will now be described.

According to various embodiments, a heavy-metal removal system that removes heavy metals from a solution containing heavy metals may include a containment vessel having a vessel inlet and a vessel outlet in fluidic communication with the vessel inlet. The heavy-metal removal system may further include at least one solid-supported trithiol compound having formula (I), as described above, in which X is a solid support, R is a linker moiety, and n≥1. The filtration system may be configured such that the solution enters the containment vessel through the vessel inlet and contacts the at least one solid-supported trithiol compound before exiting the containment vessel through the vessel outlet.

In some embodiments, the filtration systems may include a filtration apparatus, as described below with reference to FIGS. 1, 2A, and 2B. In such embodiments, the containment vessel is a filter housing 10; the vessel inlet is a filter inlet 20; the vessel outlet is a filter outlet 30, and the at least one solid-supported trithiol compound is present as an active compound 70 in a filter medium. In other embodiments, the filtration systems may be configured as batch systems, as described below with reference to FIG. 3. In such embodiments, the containment vessel may be any suitably sized holding vessel, such as an industrial-sized vessel for large-scale removal of heavy metals from water; the vessel inlet is an inlet to the holding vessel; and the vessel outlet is an outlet from the holding vessel.

Referring to FIG. 1, a filtration system configured as a filtration apparatus 100 may include a filter housing 10, a filter inlet 20, and a filter outlet 30. The filter housing 10 may be a single sealed piece or may have an end capable of being opened or closed, such as by filter cap 40. The filter housing 10 may be made from any material commonly used to make industrial or household filters such as metals or hard plastics, for example. The filter inlet 20 and the filter outlet 30 may have any desired profile for fluidically connecting the filtration apparatus 100 to an inlet stream of unprocessed solution and an outlet stream of filtered solution.

In general, in the filtration apparatus 100, the filter inlet 20 is in fluidic communication with the filter outlet 30, and the filter housing 10 contains a filter medium that is or contains at least one compound having formula (I), as described above. The at least one compound having formula (I) is provided in the filter housing 10 and is arranged or configured therein such that solution entering the filter housing 10 through the filter inlet necessarily contacts, is exposed to, or passes through, the at least one compound having formula (I) before the solution exits the filter housing 10 through the filter outlet 30. Thus, in view of this general requirement, it should be understood that the filtration apparatus 100 of FIG. 1 is intended to show only one possible configuration for filtering a solution using the compounds of formula (I) and that numerous other configurations are readily within the grasp of the person of ordinary skill The filtration apparatus 100 may be configured as a filter driven by gravity, for example, a pour-through filter; or as a filter driven by a line pressure or fed by a pump, such as in an in-line filter, for example. As non-limiting illustrative embodiments, FIGS. 2A and 2B provide two possible configurations of the filtration apparatus 100, in which a packed filter 100a of FIG. 2A and a multistage filter 100b of FIG. 2B both represent possible cross-sectional views of the same filtration apparatus 100 of FIG. 1.

Figure 2A:
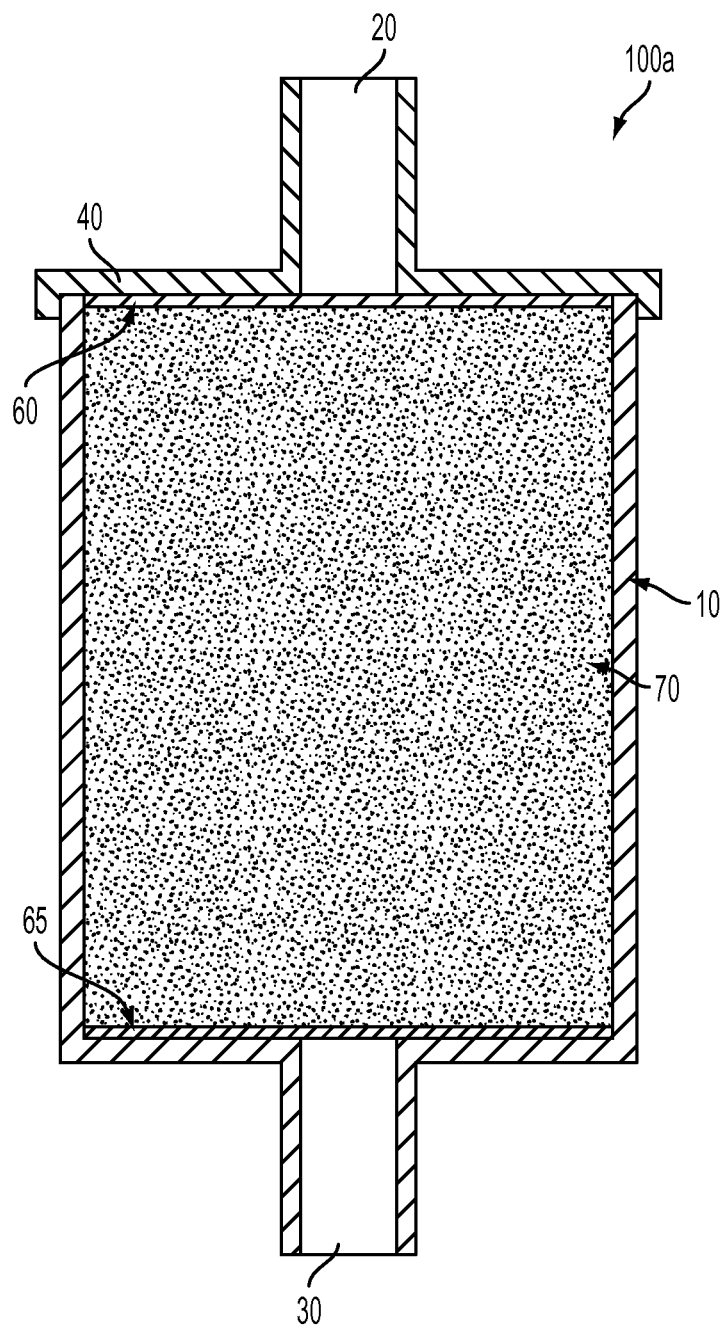
FIG. 2A is a cross-section of the filtration apparatus of FIG. 1, according to one embodiment.

In the packed filter 100a of FIG. 2A, the filter housing 10 may be packed with an active compound 70. The active compound 70 is or contains one or more compounds having formula (I), described above. The packed filter 100a may also include an inlet filter 60, an outlet filter 65, or both, which prevent the active compound 70 from flowing out of the filter housing 10 through either the filter inlet 20 or the filter outlet 30. The inlet filter 60, the outlet filter 65, or both, as applicable, may be a mesh filter such as a paper and may have a sufficiently small pore size to prevent leakage of the active compound 70 from the filter housing 10. The packed filter 100a may be used by introducing a solution containing heavy metals through the filter inlet 20, such that the solution flows into the filter housing 10 containing the active compound 70 and contacts the active compound 70. The contacting of the solution to the active compound 70 then removes all or a portion of the heavy metals from the solution. The solution then exits the filter housing 10 through the filter outlet 30.

Figure 2B:
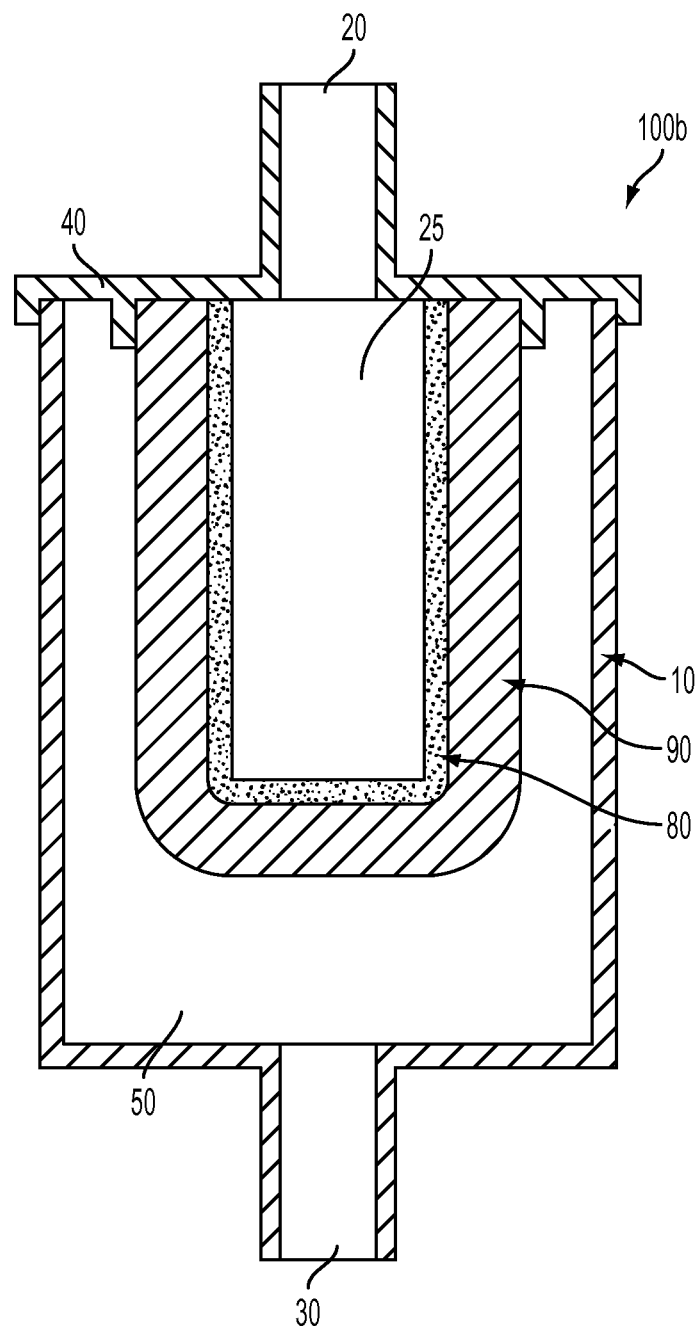
FIG. 2B is a cross-section of the filtration apparatus of FIG. 1, according to an alternative embodiment.

In the multistage filter 100b of FIG. 2B, the filter inlet 20 may open into a receiving volume 25 surrounded by an active layer 80. The active layer 80 may be or may include one or more compounds having formula (I), described above. The active layer 80 may be surrounded by and/or in contact with a secondary layer 90. The secondary layer 90 may be or may include an additional filtration material such as activated carbon or charcoal, for example. Thus, a solution containing heavy metals may be introduced into the receiving volume 25 through the filter inlet 20 to come into contact with and flow through the compound of formula (I) in the active layer 80. The solution then may flow through the secondary layer 90 into an outflow volume 50 and then may exit the filter housing 10 through the filter outlet 30.

Thus, in both the packed filter 100a of FIG. 2A and the multistage filter 100b of FIG. 2B, a solution such as waste water flows into the filter inlet 20, contacts the one or more compounds having formula (I) within the filter housing 10, and exits through the filter outlet 30. Thereby, the compounds having formula (I) may remove the heavy metals from the solution to provide a filtered solution having a substantially lower content of heavy metals than the solution that entered through the filter inlet 20.

Figure 3:
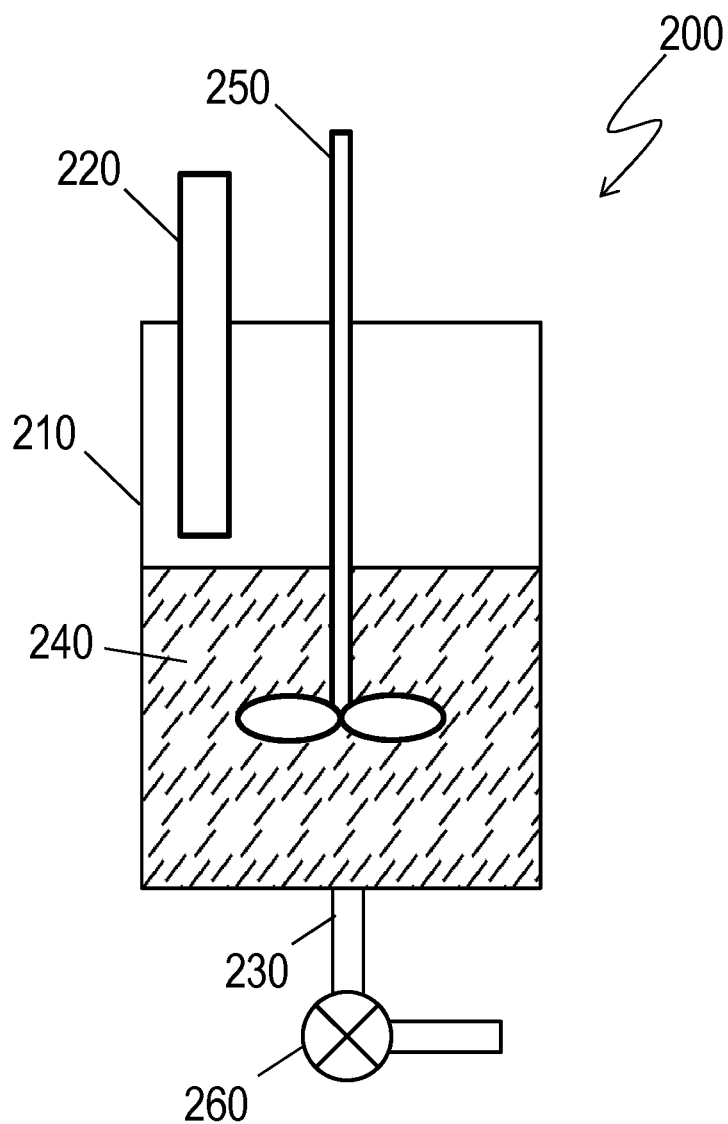
FIG. 3 is a schematic of a heavy-metal removal system configured as a batch system containing a solid-supported trithiol compound, according to embodiments herein.

Referring to FIG. 3, in further embodiments, the filtration system may be configured as a batch system 200. As shown schematically in the exemplary embodiment of a batch system 200 in FIG. 3, the batch system 200 may include a containment vessel 210 that contains an aqueous slurry 240 of the one or more compounds having formula (I). A solution containing heavy metals may be introduced into the containment vessel 210 through a vessel inlet 220. Optionally, a stifling device 250 may be present in the containment vessel 210 to intermix the heavy-metal containing solution introduced through the vessel inlet 220 with the aqueous slurry 240 in the containment vessel 210. A vessel outlet 230 of the containment vessel may be provided, through which an effluent slurry, comprising the heavy metals bound to an active compound having the formula (I), may exit for further treatment and/or disposal. The batch system 200 may further include a control valve 260, which may be positioned at the vessel outlet 230 to regulate flow rate out of the containment vessel 210.

The embodiments described herein may be further illustrated by the following non-limiting examples.

EXAMPLES

Example 1

Synthesis of N,N',N"-tris(2-sulfanylethyl)benzene-1,3,5-tricarboxamide (Compound A)

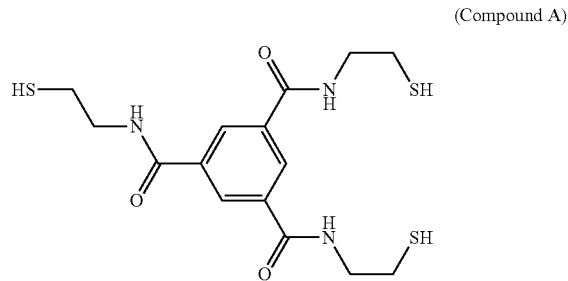 [SMILES: O=C(NCCS)c1cc(C(=O)NCCS)cc(C(=O)NCCS)c1]

(Compound A)

Trithiol Compound A (N,N',N"-tris (2-sulfanylethyl)benzene-1,3,5-tricarboxamide) was prepared according to the following synthetic route. To trimesic acid (62 g, 0.30 mol, 1 equiv.) in a 5-L, 4-neck flask with an overhead stirrer, condenser, and internal thermometer was added tetrahydrofuran (1 L). The solution was heated to 40° C., and 1,1'-carbonyldiimidazole (167.4 g, 1.03 mol, 3.5 equiv.) was added in 5 equal portions over 30 minutes. The addition of the 1,1'-carbonyldiimidazole produced a large amount of gas evolution and bubbling. The reaction mixture was stirred for 30 minutes at 40° C. The heating mantle was removed, and cysteamine hydrochloride (134.1 g, 1.18 mol, 4 equiv.) was added to the orangish solution. A dropping funnel was attached, and triethylamine (TEA) (164 mL, 1.18 mol, 4 equiv.) was added drop wise over about 30 minutes to the vigorously stirred solution. The reaction did not occur spontaneously with the addition of TEA. There was an exotherm after about 50 mL had been added, and the temperature rose to 49° C. with formation of a large amount of a white precipitate. The precipitate broke up and went into solution when all of the TEA had been added. The temperature of the reaction was kept below 50° C. during the addition of the TEA. The reaction was essentially complete after the TEA addition was completed. The reaction mixture was allowed to cool to room temperature over 30 minutes after the triethylamine addition was complete.

The reaction mixture was transferred to a 22-L workup station, and ethyl acetate (3 L) and distilled water (3 L) were added. The mixture was stirred a few minutes, then the layers were separated slowly of about 1 hour. The pink organic layer was washed with 1 N HCl (2×1.5 L) and the color disappeared. The organic layer was dried over $Na_2SO_4$, filtered and concentrated to white solid in a 5-L Morton flask. A high vacuum was attached, and the material was dried under high vacuum overnight in the morton flask. The synthesis produced 110 g of N,N',N"-tris(2-sulfanylethyl)benzene-1,3,5-tricarboxamide (Compound A), representing a yield of 96.4%.

Example 2

Preparation of Solid-Supported Trithiol Compound (Compound B)

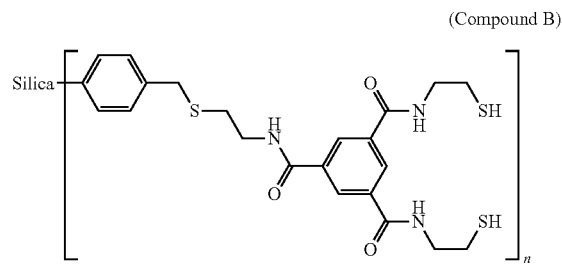

(Compound B)

A solid supported trithiol Compound B was prepared according to the following synthetic route and was used for further testing. To the trithiol Compound A (N,N',N"-tris(2-sulfanylethyl)benzene-1,3,5-tricarboxamide) of Example 1 (123.7 g, 319.2 mmol, 3 equiv.) in dimethylfuran (420 mL) under a nitrogen atmosphere were added SiliaBond® Phenylmethylchloride (80 g, 1.33 mmol/g, 106.4 mmol, 1 equiv.) and diisopropylethylamine (55.9 mL, 319.2 mmol, 3 equiv.). The reaction mixture was heated to 100° C. for 23 hours. The SiliaBond® Phenylmethylchloride was a functionalized silica having a specific surface area of 481 $m^2/g$ and an average pore volume of 0.71 mL/g. The reaction mixture then was cooled to room temperature, and the solids were filtered (Whatman #1 filter paper). The solids were washed sequentially with dimethylfuran (2×200 mL), MeOH (200 mL), distilled $H_2O$ (200 mL), MeOH (200 mL) and dichloromethane (200 mL). The silica-bound material was dried by vacuum on the filter paper. An additional wash with dichloromethane (400 mL) removed more dimethylfuran that was detectable by NMR. The silica-bound material was dried under vacuum at room temperature on a rotary evaporator to remove residual dichloromethane. A white solid was obtained with a yield 85.7 g (73%). Structural data obtained from nuclear magnetic resonance spectra ($^1$H-NMR and $^{13}$C-NMR) of the compound were consistent with that of Compound B shown above.

Example 3

Total Sulfur Loading of Compound B

Total sulfur loading of the solid-supported trithiol Compound B of Example 2 was measured by initial digestion with aqua regia at 95° C. for a minimum of 3 hours, followed by quantitative analysis of sulfur by inductively coupled plasma optical emission spectrometry (ICP-OES). The resulting sulfur concentration data was then used as a surrogate to calculate the concentration of Compound A per gram of Compound B, based on the known amount of sulfur per mol of Compound A. The same method was used to determine the sulfur and calculated Compound A concentrations when the compound is bound to arsenic or various heavy metals. TABLE 2 provides the sulfur concentration from ICP-OES analysis and the calculated concentration of Compound A per gram of Compound B alone and when bound with arsenic, mercury, cadmium or copper.

TABLE 2

| Sulfur Loading on Silica Support | | |
| --- | --- | --- |
| Control Compound | Measured mmol sulfur per gram of Compound B | Calculated mmol Compound A per gram of Compound B |
| Compound B unbound | 0.7400 ± 0.0125 | 0.2467 ± 0.0042 |
| Sample Compound | mmol sulfur per gram of Compound B | mmol Compound A per gram of Compound B |
| Compound B bound with Arsenic | 0.7139 ± 0.0152 | 0.2380 ± 0.0051 |
| Compound B bound with Mercury | 0.6914 ± 0.0080 | 0.2305 ± 0.0027 |
| Compound B bound with Cadmium | 0.7309 ± 0.0075 | 0.2436 ± 0.0025 |
| Compound B bound with Copper | 0.7351 ± 0.0119 | 0.2450 ± 0.0040 |

As shown in TABLE 2, the total amount of sulfur present per gram of Compound B prepared according to Examples 1 and 2 is the same as the total amount of sulfur present per gram of Compound B when bound to various heavy metals.

Example 4

Binding Studies of Compound B

Binding studies were performed on Compound B prepared according to Examples 1 and 2 to determine its binding efficiency for arsenic and various metals, including the divalent heavy metals of cadmium, copper, iron, lead, and zinc. The molar ratio for binding studies was 500:1 (metal:ligand).

Standard solutions (200 ppb) for binding studies were prepared. Using arsenic as the model, samples were prepared by diluting 50 μL of a stock $NaAsO_4$ solution (17.3 mg of $NaAsO_4$ in 50 mL of pH-neutral deionized water) into 50 mL of pH-neutral deionized water. Standard solutions for binding of mercury, cadmium, copper, iron, lead, and zinc were prepared similarly using the chloride salts of these metals to yield solutions with concentrations of 200 ppb.

The control samples used to assess the binding efficiency of Compound B were deionized water (method blank), untreated prepared metal samples (feed solution), and treated prepared metal samples. The treated prepared metal samples were each treated with one of the following compounds: with functionalized silica (silica phenylmethyl chloride, specifically SiliaBond® Phenylmethylchloride, as described in Example 2 above) as a negative control; with N,N',N''-tris(2-sulfanylethyl)benzene-1,3,5-tricarboxamide (Compound A prepared according to Example 1) as a trithiol compound for comparison of a compound similar to Compound B but without the functionalized silica addition; with N,N'-bis (2-sulfanylethyl)benzene-1,3-dicarboxamide (Compound D, shown below), as a positive control; or with Compound B alone.

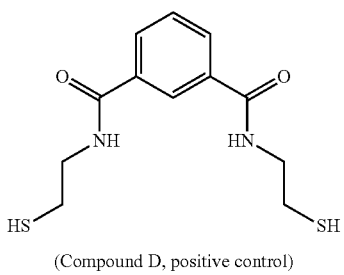 [SMILES: O=C(NCCS)c1cccc(C(=O)NCCS)c1]

(Compound D, positive control)

Active and control samples were filtered through membrane filters (0.2-μm pore size), and the resulting filtrates were analyzed by ICP-OES to determine the concentrations of unbound heavy metals remaining in solution. Thus, the arsenic or divalent metals bound to comparative Compound A, comparative Compound D, or inventive Compound B are trapped on the filter and are not detected. TABLES 3-9 below show the results of the binding studies. The percent removal was calculated as follows:

$$\% \text{ Removal} = \frac{N_U - N_T}{N_U} \times 100 \quad \text{(Equation 1)}$$

In Equation 1, $N_U$ is the concentration of heavy metal (ppm) in the untreated sample and $N_T$ is the concentration of heavy metal (ppm) in the treated sample. A reported value of 0% indicates that the actual result was manually adjusted to show no removal because the removal rate was so low as to be indistinguishable from the untreated (feed solution) sample result.

As shown in TABLE 3, the amount of arsenic present in deionized water compared with the amount of arsenic present after treating the sample with the inventive compound shows that virtually all arsenic has been removed. Further, TABLE 3 also shows that inventive Compound B outperforms Compound D and the sample treated with the unsupported trithiol Compound A.

TABLE 3

| Arsenic Removal at pH 7 | | |
|---|---|---|
| Sample | Arsenic Remaining in Solution (ppm) | % Removal by Treatment |
| Untreated (feed solution) | 1.0260 ± 0.0005 | Not applicable |
| Functionalized Silica (Negative control) | 1.0985 ± 0.0064 | 0 |
| Deionized Water (Method blank) | 0.0162 ± 0.0036 | Not applicable |
| Compound D (Comparative) | 0.0590 ± 0.0122 | 94.3% |
| Compound A (Comparative) | 0.9469 ± 0.0060 | No removal |
| Compound B (Inventive) | 0.0089 ± 0.0007 | 99.1% |

As shown in TABLE 4, the amount of mercury present in deionized water compared with the amount of mercury present after treating the sample with the inventive Compound B shows that virtually all mercury has been removed. Further, TABLE 4 also shows that the inventive Compound B outperforms Compound D and the sample treated with the unsupported trithiol Compound A.

TABLE 4

| Mercury Removal at pH 7 | | |
|---|---|---|
| Sample | Mercury Remaining in Solution (ppm) | % Removal by Treatment |
| Untreated (feed solution) | 0.5125 ± 0.0101 | Not applicable |
| Functionalized Silica (Negative control) | 0.4513 ± 0.0171 | 0 |
| Deionized Water (Method blank) | 0.0139 ± 0.0012 | Not applicable |
| Compound D (Comparative) | 0.0965 ± 0.0017 | 81.2% |
| Compound A (Comparative) | 0.0800 ± 0.0056 | 84.4% |
| Compound B (Inventive) | 0.0129 ± 0.0007 | 97.5% |

As shown in TABLE 5, the inventive Compound B outperforms comparative Compound D and the sample treated with the trithiol Compound A in removing cadmium. Compound D failed to remove any cadmium from the sample, while the inventive Compound B removed about 50%.

TABLE 5

Cadmium Removal at pH 7

| Sample | Cadmium Remaining in Solution (ppm) | % Removal by Treatment |
| --- | --- | --- |
| Untreated (feed solution) | 0.8621 ± 0.0355 | Not applicable |
| Functionalized Silica (Negative control) | 1.0158 ± 0.0301 | 0 |
| Deionized Water (Method blank) | 0.0008 ± 0.0002 | 0 |
| Compound D (Comparative) | 0.9348 ± 0.0400 | 0 |
| Compound A (Comparative) | 0.4302 ± 0.0410 | 50.1% |
| Compound B (Inventive) | 0.0639 ± 0.0083 | 93.7% |

As shown in TABLE 6, the inventive Compound B outperformed comparative Compound D in removing copper. Compound B removed 99.6% of copper, while Compound D removed only about 10.6%. The inventive Compound B performed equally as well as the sample treated with the trithiol Compound A in removing copper.

TABLE 6

Copper Removal at pH 7

| Sample | Copper Remaining in Solution (ppm) | % Removal by Treatment |
| --- | --- | --- |
| Untreated (feed solution) | 0.8862 ± 0.0278 | Not Applicable |
| Functionalized Silica (Negative control) | 1.0091 ± 0.0067 | 0 |
| Deionized Water (Method blank) | 0.0009 ± 0.0001 | 0 |
| Compound D (Comparative) | 0.7919 ± 0.0100 | 10.6% |
| Compound A (Comparative) | 0.0018 ± 0.0001 | 99.8% |
| Compound B (Inventive) | 0.0033 ± 0.0029 | 99.6% |

As shown in TABLE 7, all of the treatments failed to remove iron from solution, including the treatment with the inventive Compound B. Although not considered an environmental toxin, iron is commonly found at significant concentrations in waters of natural and industrial environments and could pose an interference with the compound's ability to bind the toxic heavy metals of interest if the binding sites were preferentially filled by iron. Thus, lack of iron binding capability is beneficial for environmental applications of the inventive Compound B.

TABLE 7

Iron Removal at pH 7

| Sample | Iron Remaining in Solution (ppm) | % Removal by Treatment |
| --- | --- | --- |
| Untreated (feed solution) | 0.8697 ± 0.0056 | Not applicable |
| Functionalized Silica (Negative control) | 1.0249 ± 0.0314 | 0 |
| Deionized Water (Method blank) | 0.0005 ± 0.0001 | Not applicable |
| Compound D (Comparative) | 0.9178 ± 0.0155 | 0 |
| Compound A (Comparative) | 0.9667 ± 0.0058 | 0 |
| Compound B (Inventive) | 0.9300 ± 0.0061 | 0 |

As shown in TABLE 8, comparative Compound D and the trithiol Compound A slightly outperform the inventive Compound B in removing lead from the sample.

TABLE 8

Lead Removal at pH 7

| Sample | Lead Remaining in Solution (ppm) | % Removal by Treatment |
| --- | --- | --- |
| Untreated (feed solution) | 0.4377 ± 0.0192 | Not applicable |
| Functionalized Silica (Negative control) | 0.6926 ± 0.0223 | 0 |
| Deionized Water (Method blank) | 0.0010 ± 0.0003 | 0 |
| Compound D (Comparative) | 0.1506 ± 0.0323 | 65.6% |
| Compound A (Comparative) | 0.1543 ± 0.0095 | 64.8% |
| Compound B (Inventive) | 0.3007 ± 0.0005 | 56.6% |

As shown in TABLE 9, comparative Compound D outperforms the inventive Compound B in removing zinc from the sample. The inventive Compound B outperforms the trithiol Compound A.

TABLE 9

Zinc Removal at pH 7

| Sample | Zinc Remaining in Solution (ppm) | % Removal by Treatment |
| --- | --- | --- |
| Untreated (feed solution) | 0.9064 ± 0.0109 | Not applicable |
| Functionalized Silica (Negative control) | 1.0092 ± 0.0386 | 0 |
| Deionized Water (Method blank) | 0.0007 ± 0.0002 | Not applicable |
| Compound D (Comparative) | 0.4097 ± 0.0188 | 54.8 |
| Compound A (Comparative) | 0.8602 ± 0.0177 | 5.1 |
| Compound B (Inventive) | 0.6912 ± 0.0213 | 31.5 |

Example 5

Binding Studies of Compound B in the Presence of Chelators

Binding studies of the Compound B prepared according to Examples 1 and 2 were performed in the presence of a model chelator, ethylenediaminetetraacetate (EDTA). EDTA is a common chelator used, for example, in the electroplating and/or circuit board industries to solubilize a wide array of metals, keeping them stable, yet inert in solution. EDTA has high formation constants for metals, including mercury, copper, lead, zinc, cadmium, and iron, and the resultant metal-EDTA complexes have strong bonds. The binding studies were performed to assess the ability of Compound B to remove metals from metal—EDTA complexes, that is, to compete with EDTA for the preferential binding and removal of copper and cadmium from solution.

An EDTA stock solution was prepared by combining 30 mL of deionized water with 0.2574 g of EDTA and adding KOH pellets, with stifling, until a clear solution resulted. The pH of the EDTA solution was adjusted down from about 12.2 to about 8.6 with dilute HCl before bringing the final volume to 50 mL. Solutions of copper (II) and cadmium (II) were prepared at pH 7 and were treated with EDTA to effect a 2:1 EDTA:metal ratio. The solutions were shaken for about 30 minutes before being combined with the inventive Compound B prepared according to Examples 1 and 2 in a 500:1 ratio of Compound B to metal. The solutions were then shaken for about 2 hours. The samples were filtered to remove particles sized 0.20 µm or larger, and the filtrates were analyzed by ICP-OES for the presence of copper and cadmium.

TABLE 10 shows the final concentrations for cadmium and copper after treatment with EDTA, and after treatment with EDTA followed by treatment with the inventive Compound B. Deionized water (method blank) was also measured to determine the detection limit of 0.002 ppm for each analyte (cadmium and copper). The percent removal rate is the amount of metal bound with EDTA that is subsequently removed from the EDTA-metal complex when treated with the inventive Compound B. Percent removal rate is calculated according to Equation 2:

$$\% \text{ Removal} = \frac{N_{EDTA} - N_{SOLUTION}}{N_{EDTA}} \times 100 \quad \text{(Equation 2)}$$

In Equation 2, $N_{EDTA}$ is the concentration of heavy metal (ppm) in the EDTA solution and $N_{SOLUTION}$ is the concentration of heavy metal (ppm) in the solution containing both EDTA and Compound B.

TABLE 10

Metal Removal in Presence of EDTA Chelator

| Test Metal | Metal (ppm) in EDTA solution | Metal (ppm) in EDTA solution after treatment with Compound B | % Removal by Treatment |
| --- | --- | --- | --- |
| Cadmium | 1.587 ± 0.047 | 0.070 ± 0.001 | 95.6 |
| Copper | 1.507 ± 0.097 | 0.002 ± 0.000 | 99.9 |

As shown in TABLE 10, cadmium and copper preferentially bind to the inventive Compound B over EDTA. The inventive Compound B removes over 95% of cadmium from the EDTA-Cd complex, and essentially all of the copper from the EDTA-Cu complex.

Example 6

Leaching Studies of Compound B

Leaching studies were performed to assess bonding strength of arsenic or the heavy metals (mercury, cadmium, and copper) to the inventive Compound B at pH 5, 7, and 9. Complexes of the inventive Compound B were prepared using NaAsO₄, HgCl₂, CdCl₂, or CuCl₂ to form arsenic, mercury, cadmium, and copper complexes with Compound B, respectively. Using arsenic as the model for the preparation of these compounds for the leaching studies, 667 mg of NaAsO₄ was dissolved in 50 mL of pH-neutral deionized water. The inventive Compound B (10.5 g) was added to the arsenic solution and was stirred at room temperature for two hours to form the arsenic complex with Compound B. The admixture of the arsenic complex with Compound B was filtered through Whatman No. 1 filter paper, was rinsed three times with pH-neutral deionized water (50 mL each), and was further rinsed three times with 95% ethanol (50 mL each). The arsenic complex with Compound B was air-dried for 48 hours at room temperature to form a free-flowing powder of the arsenated compound.

For leaching, screw-capped 50-mL polypropylene tubes were filled with a portion of the arsenic complex with Compound B and a sufficient volume of water buffered to pH 5, 7, or 9 to yield an As concentration of approximately 100 ppm. The metallated mercury, cadmium, and copper complexes with Compound B were prepared similarly and were each adjusted with water buffered to pH 5, 7, or 9 to concentrations of approximately 90 ppm Hg, approximately 50 ppm Cd, and approximately 80 ppm Cu.

The leaching studies were performed in sealed 50-mL polypropylene tubes in an incubator-shaker at 30° C. (with shaking). Triplicate samples were run for each pH per time period. Samples were filtered through membrane filters (0.2-μm pore size) and the resulting filtrate was analyzed by ICP-OES to determine the amount of arsenic or heavy metal leached from the arsenated or metallated complex of Compound B into solution. The percent leached was calculated according to Equation 3:

$$\% \text{ Leached} = \frac{N_{AVAIL} - N_{SOLUTION}}{N_{AVAIL}} \times 100 \quad \text{(Equation 3)}$$

In Equation 3, $N_{AVAIL}$ is the total amount of available heavy metal and $N_{SOLUTION}$ is the concentration of heavy metal measured in the filtered solution. The results of the leaching studies are provided in TABLES 11-14.

In the arsenic study, the total available arsenic for leaching was 96.82 ppm±7.51 ppm. The amount of arsenic removed by leaching is shown in TABLE 11. The highest amount of arsenic leached was at pH 9 and showed a steady increase with time. Slightly lesser amounts of arsenic was leached at pH 5 and pH 7, but increased with time at these pH levels as well.

TABLE 11

Leaching of Arsenic

| | pH 5 | | pH 7 | | pH 9 | |
| --- | --- | --- | --- | --- | --- | --- |
| Week | ppm As | % Leached | ppm As | % Leached | ppm As | % Leached |
| 1 | 23.06 ± 0.28 | 23.8 | 23.96 ± 0.37 | 24.8 | 27.76 ± 1.07 | 28.7 |
| 2 | 25.06 ± 0.69 | 25.9 | 27.13 ± 0.16 | 28.0 | 30.87 ± 1.16 | 31.9 |
| 3 | 26.30 ± 0.53 | 27.2 | 28.75 ± 0.41 | 29.7 | 32.91 ± 0.67 | 34.0 |
| 4 | 27.60 ± 0.90 | 28.5 | 29.12 ± 0.49 | 30.1 | 34.64 ± 0.97 | 35.8 |
| 5 | 27.57 ± 1.02 | 28.5 | 29.43 ± 0.50 | 30.4 | 34.96 ± 0.92 | 36.1 |

In the mercury study, the total amount of available mercury for leaching was 87.31 ppm±0.03 ppm. The amount of mercury removed by leaching is shown in TABLE 12. The highest concentrations of leached mercury occurred at pH 5 and showed a decrease in mercury concentration with time. About half of the amount of mercury leached at pH 5 was also leached at pH 7 and decreased with time. Slightly more mercury was leached at pH 9 than at pH 7, and the concentration also decreased with time. Thus, no discernable trend in per cent leaching was noted as the pH increased.

TABLE 12

| | Leaching of Mercury | | | | | |
|---|---|---|---|---|---|---|
| | pH 5 | | pH 7 | | pH 9 | |
| Week | ppm Hg | % Leached | ppm Hg | % Leached | ppm Hg | % Leached |
| 1 | 10.53 ± 0.07 | 12.1 | 5.13 ± 0.39 | 5.9 | 8.22 ± 0.21 | 9.4 |
| 2 | 9.94 ± 0.11 | 10.9 | 3.59 ± 0.30 | 4.1 | 5.00 ± 0.26 | 5.7 |
| 3 | 8.43 ± 0.14 | 9.7 | 3.20 ± 0.42 | 3.7 | 3.90 ± 0.05 | 4.5 |
| 4 | 7.77 ± 0.08 | 8.9 | 2.88 ± 0.31 | 3.3 | 3.08 ± 0.16 | 3.5 |
| 5 | 7.93 ± 0.14 | 9.1 | 2.81 ± 0.23 | 3.2 | 2.87 ± 0.06 | 3.3 |

In the cadmium study, the total amount of available cadmium for leaching was 44.29 ppm±7.26 ppm. The amount of cadmium removed by leaching is shown in TABLE 13. The highest concentrations of leached cadmium occurred at pH 5 and showed a steady increase with time. Slightly less than half of the amount of cadmium leached at pH 5 was also leached at pH 7 and increased with time. Only a small amount of cadmium leached at pH 9 with no discernable increasing or decreasing trend with time.

TABLE 13

| | Leaching of Cadmium | | | | | |
|---|---|---|---|---|---|---|
| | pH 5 | | pH 7 | | pH 9 | |
| Week | ppm Cd | % Leached | ppm Cd | % Leached | ppm Cd | % Leached |
| 1 | 8.87 ± 0.24 | 20.0 | 3.75 ± 0.08 | 8.5 | 0.40 ± 0.03 | 0.9 |
| 2 | 10.45 ± 0.13 | 23.6 | 4.51 ± 0.09 | 10.2 | 0.51 ± 0.06 | 1.2 |
| 3 | 11.19 ± 0.27 | 25.3 | 5.05 ± 0.14 | 11.4 | 0.65 ± 0.11 | 1.5 |
| 4 | 11.81 ± 0.12 | 26.7 | 5.26 ± 0.07 | 11.9 | 0.70 ± 0.17 | 1.6 |
| 5 | 12.27 ± 0.42 | 27.7 | 5.54 ± 0.02 | 12.3 | 0.57 ± 0.02 | 1.3 |

In the copper study, the total amount of available copper for leaching was 79.15 ppm±7.46 ppm. The amount of copper removed by leaching is shown in TABLE 14. The greatest copper leaching occurred at pH 5 and showed a steady increase with time. Significantly less copper was leached at pH 7, but also increased with time. Only a slight amount of copper was leached at pH 9 and showed a slight decrease with time.

TABLE 14

| | Leaching of Copper | | | | | |
|---|---|---|---|---|---|---|
| | pH 5 | | pH 7 | | pH 9 | |
| Week | ppm Cu | % Leached | ppm Cu | % Leached | ppm Cu | % Leached |
| 1 | 47.50 ± 0.51 | 60.0 | 3.51 ± 0.88 | 4.4 | 0.97 ± 0.01 | 1.2 |
| 2 | 52.56 ± 0.47 | 66.4 | 4.10 ± 0.06 | 5.2 | 0.81 ± 0.04 | 1.0 |
| 3 | 55.26 ± 0.08 | 69.8 | 4.06 ± 0.08 | 5.1 | 0.72 ± 0.03 | 0.9 |
| 4 | 57.54 ± 0.65 | 72.7 | 4.14 ± 0.17 | 5.2 | 0.64 ± 0.03 | 0.8 |
| 5 | 58.99 ± 0.25 | 74.5 | 4.12 ± 0.16 | 5.2 | 0.58 ± 0.02 | 0.7 |

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

What is claimed is:

1. A solid-supported trithiol compound having formula (I):

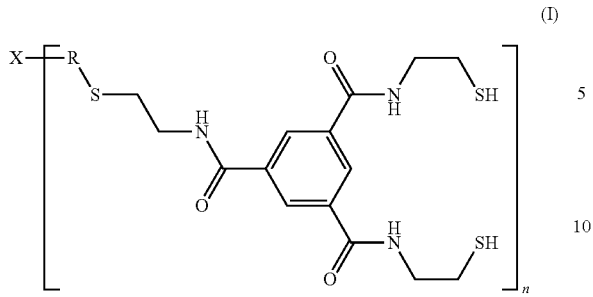

(I)

where X is a solid support, R is a linker moiety, and n≥1.

2. The solid-supported trithiol compound of claim 1, wherein R is an optionally substituted hydrocarbon group containing from 1 to 20 carbon atoms, in which one or more carbon atoms is optionally replaced by a nitrogen atom or an oxygen atom.

3. The solid-supported trithiol compound of claim 1, wherein R is chosen from:

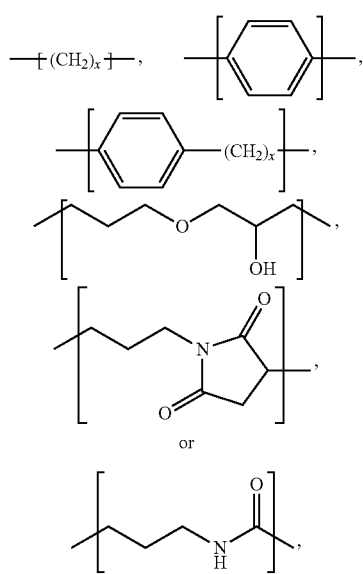

where x is from 1 to 10.

4. The solid-supported trithiol compound of claim 1, wherein the solid support X is chosen from silica, silica beads, functionalized silica, alumina, alumina beads, polyethylene, polypropylene, polyvinylchloride, polystyrene, polystyrene copolymers, polyacrylamides, polymethacrylates, polysaccharides, phenolic resins, polymer beads, and carbon.

5. The solid-supported trithiol compound of claim 1, wherein the solid support X is chosen from silica, silica beads, functionalized silica, alumina, or polysytrene.

6. The solid-supported trithiol compound of claim 1, wherein the solid support X is chosen from silica, silica beads, or functionalized silica.

7. The solid-supported trithiol compound of claim 1, wherein:

the solid support X is chosen from silica, silica beads, or functionalized silica; and the linker moiety R is chosen from:

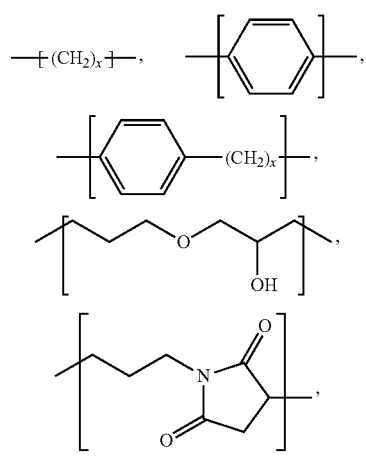

where x is from 1 to 10.

8. The solid-supported trithiol compound of claim 1, chosen from:

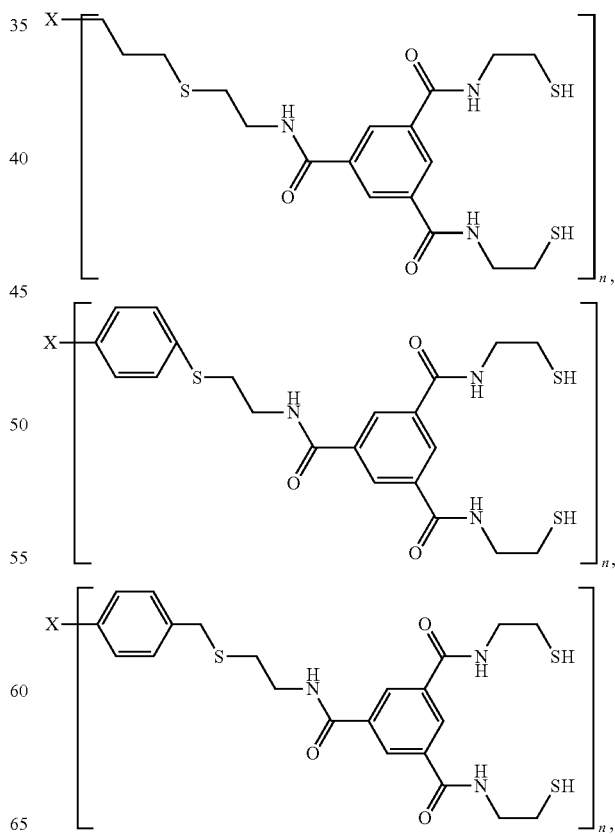

-continued

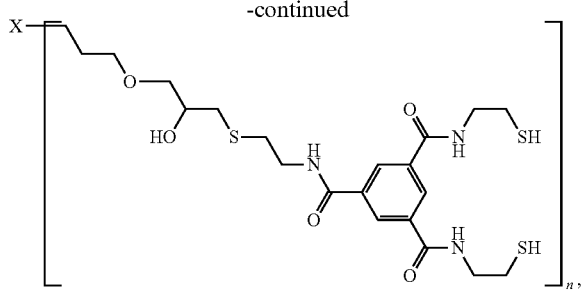

or

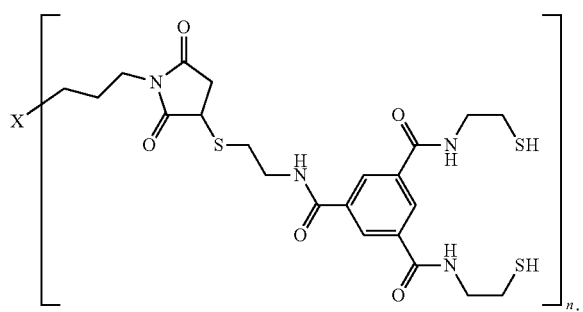

9. The solid-supported trithiol compound of claim 8, wherein the solid support X is chosen from silica, silica beads, or functionalized silica.

10. The solid-supported trithiol compound of claim 1, wherein:
the solid-supported trithiol compound comprises

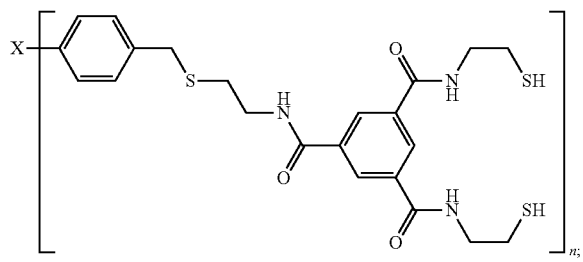

and
the solid support X is chosen from silica, silica beads, or functionalized silica.

11. A method for removing heavy metals from a solution containing the heavy metals, the method comprising:
contacting the solution with a solid-supported trithiol compound having formula (I):

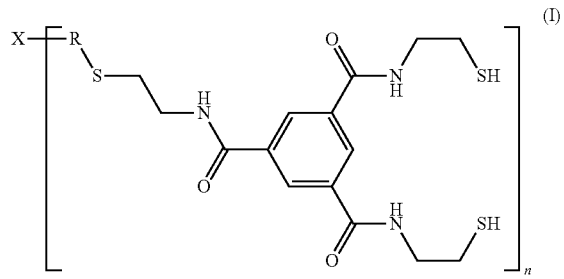

in which X is a solid support, R is a linker moiety, and n≥1; and forming complexes of the heavy metals with the compound of formula (I) to remove the heavy metals from the solution.

12. The method of claim 11, wherein the heavy metals are chosen from mercury, arsenic, cadmium, copper, lead, zinc, and combinations thereof.

13. The method of claim 12, wherein the solid support X is chosen from silica, silica beads, functionalized silica, alumina, alumina beads, polyethylene, polypropylene, polyvinylchloride, polystyrene, polystyrene copolymers, polyacrylamides, polymethacrylates, polysaccharides, phenolic resins, polymer beads, and carbon.

14. The method of claim 12, wherein:
the solid support X is chosen from silica, silica beads, or functionalized silica; and
the linker moiety R is chosen from:

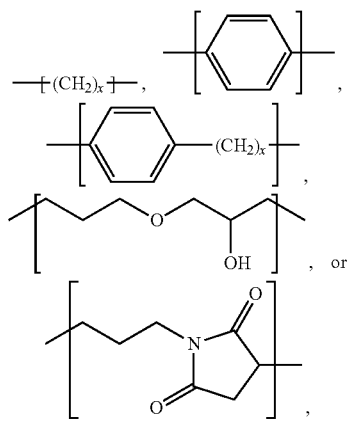

where x is from 1 to 10.

15. The method of claim 12, wherein the solid-supported trithiol compound is

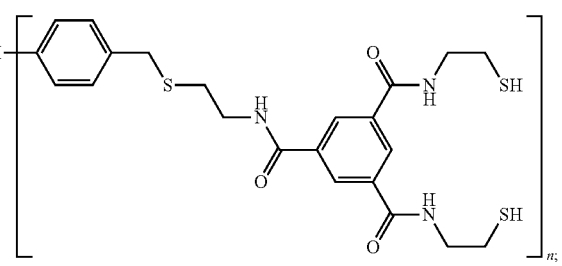

and
the solid support X is chosen from silica, silica beads, or functionalized silica.

16. The method of claim 11, further comprising:
adding a chelator to the solution before contacting the solution with the solid-supported trithiol compound, whereby the chelator forms complexes of the chelator with the heavy metals, and when the solution contacts the solid-supported trithiol compound, the heavy metals in the complexes preferentially bind to the solid-supported trithiol compound.

17. The method of claim 16, wherein the chelator is chosen from ethylenediamine-tetraacetic acid, N-(hydroxyethyl)-ethylenediaminetriacetic acid, ethylene glycol tetraacetic acid, diethylenetriaminepentaacetic acid, nitrilotriacetic acid, diethylenetriamine penta(methylene phosphonic acid), dimercaptosuccinic acid, 2,3-dimercapto-1-propane-sulfonic acid, or combinations thereof.

18. A heavy-metal removal system that removes heavy metals from a solution containing the heavy metals, the removal system comprising:
   a containment vessel having a vessel inlet and a vessel outlet in fluidic communication with the vessel inlet;
   at least one solid-supported trithiol compound having formula (I):

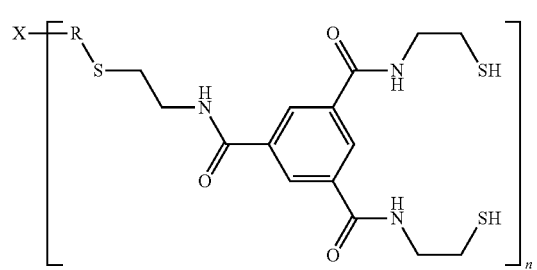

(I)

in which X is a solid support, R is a linker moiety, and $n \geq 1$,
wherein the filtration system is configured such that the solution enters the containment vessel through the vessel inlet and contacts the at least one solid-supported trithiol compound exiting the containment vessel through the vessel outlet.

19. The heavy-metal removal system of claim 18, wherein:
   the solid-supported trithiol compound comprises

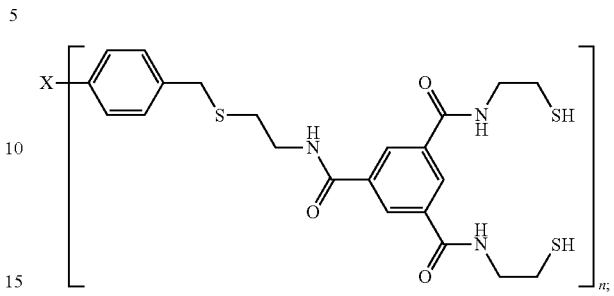

and
   the solid support X is chosen from silica, silica beads, or functionalized silica.

20. The heavy-metal removal system of claim 18, wherein the heavy-metal removal system is configured as a batch system in which the solution contacts an aqueous slurry of the least one solid-supported trithiol compound in the containment vessel, or wherein the heavy-metal removal system is configured as a filtration apparatus in which the at least one solid-supported trithiol compound is present in a filter medium in the containment vessel.

* * * * *